United States Patent [19]

Van Endschot et al.

[11] Patent Number: 4,961,214

[45] Date of Patent: Oct. 2, 1990

[54] X-RAY EXAMINATION APPARATUS COMPRISING A BALANCED SUPPORTING ARM

[75] Inventors: Johannes G. Van Endschot; Adrianus A. J. Van Der Vegt, both of Eindhoven, Netherlands

[73] Assignee: U. S. Philips Corporation, New York, N.Y.

[21] Appl. No.: 370,213

[22] Filed: Jun. 22, 1989

[30] Foreign Application Priority Data

Jul. 11, 1988 [NL] Netherlands ............... 8801750

[51] Int. Cl.$^5$ .............................. H05G 1/02
[52] U.S. Cl. ................................ 378/197; 378/196
[58] Field of Search ............ 378/195, 196, 197, 198

[56] References Cited

U.S. PATENT DOCUMENTS 3,281,598 10/1966 Holstein ..................... 378/179
3,892,967 7/1975 Grady et al.
4,363,128 12/1982 Grady et al. ................. 378/197

FOREIGN PATENT DOCUMENTS 1175032 12/1969 United Kingdom .

Primary Examiner—Craig E. Church
Attorney, Agent, or Firm—William Squire

[57] ABSTRACT

An X-ray examination apparatus for irradiating an object in different directions comprises a C-shaped support whereto there are secured an X-ray source, an X-ray detector and a counterweight. The counterweight is situated at the end of the arm which also carries the X-ray detector. The movement of the counterweight is such that for all positions of the X-ray detector the center of gravity of the support, the X-ray source, the X-ray detector and the counterweight is situated in the point of intersection of the axes of rotation (the isocenter). As a result, the support is continuously balanced and manual adjustment of the support is possible. Balancing is enhanced by a cast and hence light C-shaped support.

7 Claims, 1 Drawing Sheet

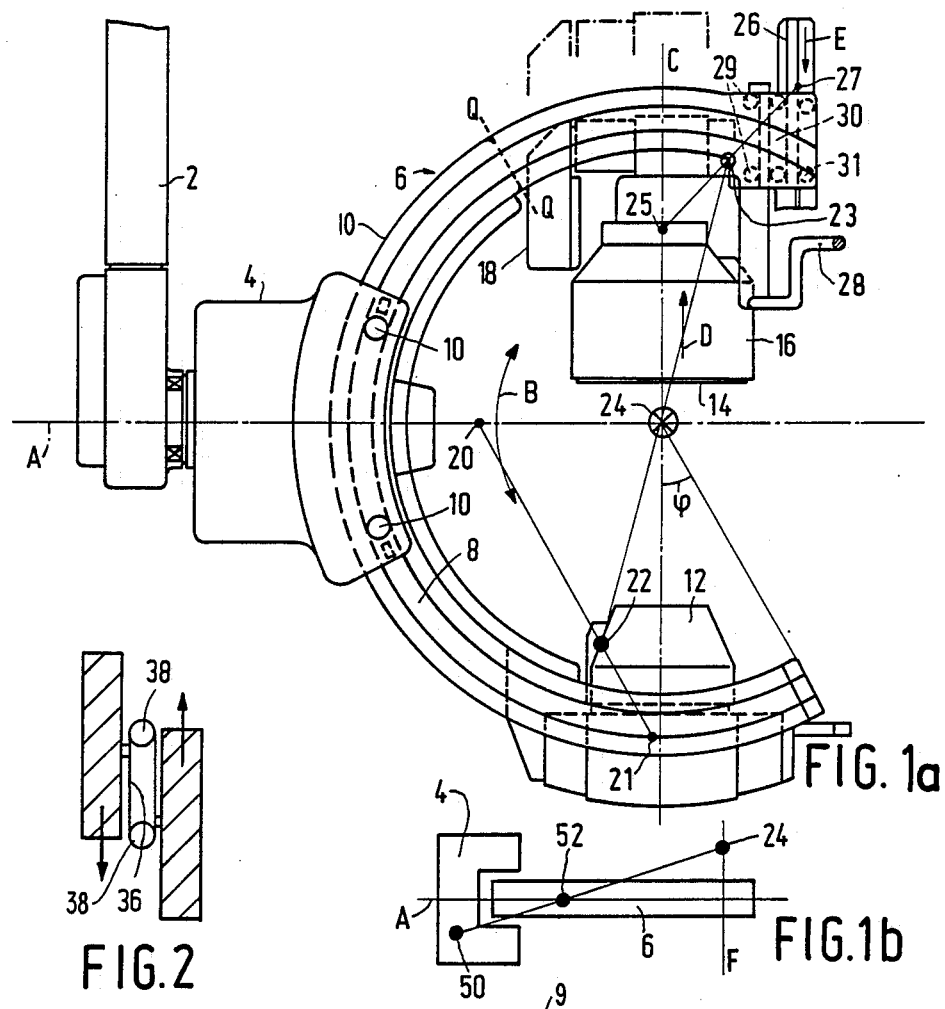
FIG.1a
FIG.2
FIG.1b
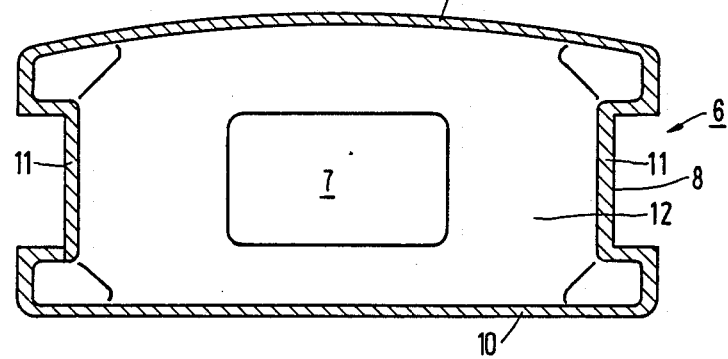
FIG.3

X-RAY EXAMINATION APPARATUS COMPRISING A BALANCED SUPPORTING ARM

The invention relates to an X-ray examination apparatus, comprising a vertical column, a sleeve which is connected to the column and which is rotatable about a first horizontal axis, and a C-shaped support which is carried by the sleeve and which is movable in the sleeve about a second axis which intersects the first axis at right angles, said C-shaped support accommodating an X-ray source at a first end and an X-ray detector at a second end, which X-ray detector is movable along a central ray of an X-ray beam to be emitted by the X-ray source.

An X-ray examination apparatus for irradiating an object in different directions is known from U.S. Pat. No. U.S. 3,281,598.

In an X-ray examination apparatus described therein combined rotation of the X-ray source and the X-ray detector, connected to a two-armed support, takes place about three axes which intersect one another at right angles in one point (the iso-centre) which is situated between the X-ray source and the X-ray detector. The known X-ray examination apparatus, however, is not balanced and the locking in positions in which the two-armed support is rotated out of a vertical plane about a first horizontal axis is provided by an electric motor and a gearwheel transmission. Movement of the two-armed support in the sleeve under the influence of the force of gravity is prevented by an electric motor which locks the arm in the sleeve for a given irradiation direction. Manual adjustment of the direction of irradiation, however, is obstructed thereby. In order to prevent the non-balanced, comparatively heavy X-ray detector, for example an X-ray image intensifier tube, from colliding with the support or an object to be examined upon displacement along the central ray, for example for adjusting an enlargement, the X-ray examination apparatus usually comprises protection mechanism.

It is an object of the invention to provide a compact X-ray examination apparatus of comparatively simple construction for irradiating an object from different directions, in which an X-ray source and an X-ray detector are arranged opposite one another, and in which the positions of the X-ray source and the direction of irradiation are manually adjustable without substantial effort.

To achieve this, an X-ray examination apparatus of the kind set forth in accordance with the invention is characterized in that a shift of a centre of gravity of the X-ray detector which occurs upon displacement of the X-ray detector along the central ray is substantially compensated for by way of a counterweight which is secured to the second end of the support and whose direction of movement opposes that of the X-ray detector, in that a common centre of gravity of the support, the X-ray source, the X-ray detector and the counterweight is situated on the second axis for an adjustable range of distances between the X-ray detector and the X-ray source, and in that a common centre of gravity of the sleeve, the support, the X-ray detector, the X-ray source and the counterweight is situated on the first horizontal axis for an adjustable range of distances between the X-ray detector and the X-ray source.

It is to be noted that the balancing of the motion of the X-ray detector by means of a counterweight which moves in the opposite direction is known per se from U.S. Pat. No. 3,892,967.

In the apparatus described in the cited Patent Specification a two-armed support is formed by a pivotable parallellogram construction comprising an X-ray source and an X-ray detector which are situated opposite one another on two long projecting arms. The counterweight moves, via a pulley construction, along one of the short side arms interconnecting the projecting arms in the parallellogram construction. For the balancing of such an X-ray examination apparatus, correct adaptation of weight and position of the X-ray source, the X-ray detector, the balancing weight and the support is less critical than for the balancing of a C-shaped support. The common centre of gravity of all parts can be situated in a position on the first axis of rotation by adding balancing weights to the parallellogram construction. No additional balancing weights may be added to the C-shaped support which must be capable of moving freely in the sleeve, and adaptation of the centres of gravity of the C-shaped support, the X-ray source, the X-ray detector and the balancing weight so that the common centre of gravity thereof is situated on the second axis of rotation is essential.

A preferred embodiment of an X-ray examination apparatus in accordance with the invention is characterized in that the C-shaped support is formed by a tubular profile provided with two running surfaces on an outer side, which profile comprises internal partitions, said profile, running surfaces and partitions being formed by a single casting having a wall thickness of between approximately 8 and 5 mm.

By casting the support as an integral unit having a comparatively small wall thickness, the number of operations required for manufacturing the support is reduced; moreover, the small wall thickness of the casting enables fast dissipation of heat from the casting after the casting process, so that a comparatively light and high-quality casting is obtained as a result of the fast cooling. Because of the comparatively large saving in weight enabled by the castinq process, the load exerted on the sleeve, the C-shaped support itself and the vertical suspension is comparatively low, and facilitates balancing.

The invention will be described in detail hereinafter with reference to the accompanying drawing; therein FIG. 1a is a side elevation of an X-ray examination apparatus, FIG. 1b is a diagrammatic plan view of an X-ray examination apparatus, FIG. 2 diagrammatically illustrates the movement of the X-ray detector and the counterweight, and FIG. 3 is a cross-sectional view of a cast C-shaped support.

FIG. 1a shows a vertical column 2 and a sleeve 4 secured thereto. The sleeve 4 is rotatable about an axis A and supports a two-armed support 6 (in this case in the form of a C-arc). The support 6 is provided on both sides with slots 8 (only one of which is visible in the Figure) in which there are arranged bearing wheels 10, and which are movable in the sleeve 4 in the direction of arrow B. At one end of the support 6 there is situated an X-ray source 12 which emits an X-ray beam which is incident on an entrance screen 14 of an X-ray image intensifier tube 16. The X-ray image intensifier tube 16 converts an X-ray image of a body located between the X-ray source 12 and the X-ray detector 16 into a visible image which is detected by means of a video camera 18. The centre of gravity of the support 6 is situated in a position 20, the common centre of gravity of the X-ray source 12 and the support 6 being situated in a point 22. The X-ray image intensifier tube 25 has a centre of gravity in a position 25, a counterweight 26 having a centre of gravity in a position 27. Movement of the X-ray image intensifier tube 16 parallel to the axis C is guided along a centre ray of the source 12 by wheels 29, transmission means 30 transferring to the counterweight 26 a motion of the X-ray image intensifier tube in the opposite direction. A movement of the counterweight 26 is guided by wheels 31. When the X-ray image intensifier tube 16 is moved in the direction of an arrow D by means of a grip 28 connected to the X-ray image intensifier tube, the counterweight 26 coupled to the X-ray image intensifier tube is moved in the direction of an arrow E. As a result, the common centre of gravity of the X-ray image intensifier tube and the counterweight remains in the position 23 and the common centre of gravity of the support 6, the X-ray source 12 and the combination formed by the X-ray image intensifier tube and the counterweight remains in the position 24 which is situated on the second axis of rotation which extends perpendicularly to the plane of drawing. Because the centre of gravity remains situated on the second axis of rotation during movement of the arm 6 in the direction of the arrow B, little effort will be required for this operation. The common centre of gravity of the sleeve 4, the arm 6, the X-ray source 12 and the combination formed by the image intensifier tube and the counterweight is situated on the axis A, so that the X-ray examination apparatus is balanced during rotation about the axis A.

FIG. 1b is a plan view of the sleeve 4 and the support 6. When the common centre of gravity of the support, the X-ray detector and the counterweight is situated in a position 24 on the second axis F, the centre of gravity of the sleeve 4 is situated in a position 50 so that the common centre of gravity is situated in a position 52 on the first horizontal axis A.

FIG. 2 diagrammatically illustrates the coupling of the movement of the X-ray image intensifier tube and the counterweight. For example, via a drive belt or chain 36 which extends in a closed loop around two pulleys 38 and whereto the X-ray image intensifier tube as well as the counterweight are secured, the movement of the X-ray image intensifier tube is transferred to the counterweight in the opposite direction.

FIG. 3 is a cross-sectional view of C-shaped support 6, taken along a line Q-Q, in FIG. 1a. The wall thickness of an inner side 9 and an outer side 10 of the casting amounts to 5 mm, the thickness of the side walls being 8 mm. As a result of the U-shaped recessed running surfaces 11 and the curvature of the inner side 9, the profile has an optimum stiffness to weight ratio. A number of partitions 12 are arranged at regular distances from one another in the support 6 and have a wall thickness of, for example, 6 mm. The partitions 12 have an 7 opening for the passage of cables, for example, for powering the X-ray source or for transporting X-ray detector signals. After completion of the casting, holes will be present in the running surfaces 11 at areas where casting cores for securing and correct positioning project through the wall 11. After casting, these holes are closed by welding and the surface of the running faces 11, being formed with a high casting quality and having a comparatively low porosity, are subjected to a finishing operation, if necessary. The outer sides of the walls 9 and 10 may be sandblasted. The support 6 is preferably made of cast AlSi10Mg(CU)WA or AlZn10Si8Mg or equivalent, comparatively light materials. AlZn10Si8Mg has the advantage of cold hardening, so that it is not necessary to harden the C-shaped supporting arm in, for example an oven.

What is claimed is:

1. An X-ray examination apparatus including a column, a sleeve connected to the column and rotatable about a first horizontal axis, a C-shaped support movably secured to the sleeve for rotation about a second axis which intersects the first axis at right angles, said sleeve having a center of gravity offset from said first and second axes, an X-ray source secured to the support at a first support end and an X-ray detector secured to the support at a second support end, the X-ray detector being movable along a central ray of an X-ray beam emitted by the source, the combination therewith comprising:

a counterweight movably secured to said second end;
means for coupling the counterweight to said detector such that a shift in the center of gravity of the X-ray detector upon displacement of the detector shifts the position of the counterweight; and
means for compensating for the shift in center of gravity of the detector including means for positioning the combined center of gravity of the support, X-ray source, X-ray detector and counterweight on the second axis over an adjustable range of distances of the detector relative to the source and for positioning the combined center of gravity of the sleeve, support, X-ray detector, X-ray source and counterweight on the first axis over said adjustable range of distances.

2. An X-ray examination apparatus as claimed in claim 1, characterized in that the C-shaped support is formed by a tubular profile provided with two running surfaces on an outer side, which profile comprises internal partitions, said profile, running surfaces and partitions being formed by a single casting having a wall thickness of between approximately 8 and 5 mm.

3. An X-ray examination apparatus as claimed in claim 1, characterized in that the X-ray detector comprises image intensifier tube.

4. An X-ray examination apparatus as claimed in claim 2, characterized in that the C-shaped support contains one of the alloys G-AlSi10Mg(CU)WA and G-AlZn10Si8Mg.

5. An X-ray examination apparatus including a column, a sleeve connected to the column and rotatable about a first horizontal axis, a C-shaped support movably secured to the sleeve for rotation about a second axis which intersects the first axis at right angles, said sleeve having a center of gravity offset from said first and second axes, an X-ray source secured to the support at a first support end and an X-ray detector movably secured to the support at a second support end, the combination therewith comprising:

a counterweight movably secured to said support; and
means for coupling the counterweight to said detector such that a shift in the center of gravity of the X-ray detector upon displacement of the detector shifts the position of the counterweight, said counterweight being so constructed and positioned to compensate for the shift in center of gravity of the detector by maintaining the combined center of gravity of the support, X-ray source, X-ray detector and counterweight on the second axis over an adjustable range of distances of shift of positions of the detector relative to the source and by maintaining the combined center of gravity of the sleeve, support, X-ray detector, X-ray source and counterweight on the first axis over said adjustable range of distances.

6. The apparatus of claim 5 wherein said counterweight comprises a weight secured for translation in response to the displacement of said detector for maintaining the combined center of gravity of said weight and said detector in fixed position relative to the support regardless the displacement of said detector.

7. The apparatus of claim 6 wherein the combined center of gravity of the detector and weight are offset from said first axis to maintain the combined center of gravity of the sleeve therewith on said first axis.

* * * * *